US009347090B2

(12) United States Patent
Kornman et al.

(10) Patent No.: US 9,347,090 B2
(45) Date of Patent: *May 24, 2016

(54) METHOD FOR DETERMINING SEVERITY AND PROGRESSION OF PERIODONTAL DISEASE

(71) Applicant: Interleukin Genetics, Inc., Waltham, MA (US)

(72) Inventors: Kenneth Kornman, Waltham, MA (US); Xiaodong Wu, Needham, MA (US); Hwa-Ying Wang, Palo Alto, CA (US); John Rogus, North Andover, MA (US)

(73) Assignee: Interleukin Genetics, Inc., Waltham, MA (US)

( * ) Notice: Subject to any disclaimer, the term of this patent is extended or adjusted under 35 U.S.C. 154(b) by 132 days.

This patent is subject to a terminal disclaimer.

(21) Appl. No.: 13/962,637

(22) Filed: Aug. 8, 2013

(65) Prior Publication Data

US 2013/0337448 A1 Dec. 19, 2013

Related U.S. Application Data

(63) Continuation of application No. 13/316,198, filed on Dec. 9, 2011.

(60) Provisional application No. 61/421,628, filed on Dec. 9, 2010, provisional application No. 61/452,157, filed on Mar. 13, 2011.

(51) Int. Cl.
*C12Q 1/68* (2006.01)
*C07H 21/04* (2006.01)

(52) U.S. Cl.
CPC ............ *C12Q 1/6827* (2013.01); *C12Q 1/6883* (2013.01); *C12Q 2600/156* (2013.01); *C12Q 2600/172* (2013.01); *G01N 2800/18* (2013.01)

(58) Field of Classification Search
None
See application file for complete search history.

(56) References Cited

U.S. PATENT DOCUMENTS

| | | | |
|---|---|---|---|
| 4,582,788 | A | 4/1986 | Erlich |
| 4,666,828 | A | 5/1987 | Gusella |
| 4,801,531 | A | 1/1989 | Frossard |
| 5,110,920 | A | 5/1992 | Erlich |
| 5,268,267 | A | 12/1993 | Smith |
| 5,272,057 | A | 12/1993 | Smulson et al. |
| 5,328,829 | A | 7/1994 | Stashenko |
| 5,686,246 | A | 11/1997 | Kornman et al. |
| 6,130,042 | A | 10/2000 | Diehl et al. |
| 2004/0152124 | A1 | 8/2004 | Duff et al. |
| 2005/0282198 | A1 | 12/2005 | Duff et al. |
| 2008/0118920 | A1 | 5/2008 | Duff et al. |
| 2010/0129798 | A1 | 5/2010 | Abramson et al. |

FOREIGN PATENT DOCUMENTS

WO   WO 2005/108619   11/2005

OTHER PUBLICATIONS di Giovine, F. S. et al, "Chapter 2: Detection and population analysis of IL-1 and TNF gene polymorphisms", excerpt (from Cytokine Molecular Biology (Balkwill, F. editor, Oxford University Press, Oxford, 2000)).*
Kornman, K.S. et al. Journal of Clinical Periodontology 24:72 (1997).*
Lopez, N.J. et al. Journal of Periodontology 80(10):1590 (Oct. 2009).*
Offenbacher, S. et al. Journal of Periodontology 78:1911 (Oct. 2007).*
Chen et al. "Single Nucleotide Polymorphisms in the Human Interleukin-1B Gene Affect Transcription According to Haplotype Context." *Hum. Mol. Genetics.* 15.4(2006):519-529.
Clark et al. "Genomic Sequence for Human Prointerleukin 1 beta: Possible Evolution from a Reverse Transcribed Prointerleukin 1 alpha Gene." *Nucleic Acids Res.* 14.20(1986):7897-7914.
Clark et al. "Corrigenda: Genomic Sequence for Human Prointerleukin 1 beta: Possible Evolution from a Reverse Transcribed Prointerleukin 1 alpha Gene." *Nucleic Acids Res.* 15.2(1987):868.
Clay et al. "Novel Interleukin-1 Receptor Antagonist Exon Polymorphisms and Their Use in Allele-Specific mRNA Assessment." *Hum. Genet.* 97.6(1996):723-726.
Nicklin et al. "A Physical Map of the Region Encompassing the Human Interleukin-1α, Interleukin-1β, and Interleukin-1 Receptor Antagonist Genes." *Genomics.* 19.2(1994):382-384.
Nikolopoulos et al. "Cytokine Gene Polymorphisms in Periodontal Disease: A Meta-Analysis of 53 Studies Including 4178 Cases and 4590 Controls." *J. Clin. Periodontol.* 35.9(2008):754-767.
Nothwang et al. "Molecular Cloning of the Interleukin-1 Gene Cluster: Construction of an Integrated YAC/PAC Contig and a Partial Transcriptional Map in the Region of Chromosome 2q13." *Genomics.* 41.3(1997):370-378.
Rogus et al. "IL1B Gene Promoter Haplotype Pairs Predict Clinical Levels of Interleukin-1 β and C-Reactive Protein." *Hum. Genet.* 123(2008):387-398.
Tarlow et al. "Severity of Alopecia Areata is Associated with a Polymorphism in the Interleukin-1 Receptor Antagonist Gene." *J. Invest. Dermatol.* 103.3(1994):387-390.
Wu et al. "IL1B Genotypes Associated With Severe Peridontitis in Multiple Ethnic Populations." *The Preliminary Program for IADR/AADR/CADR 89th General Session and Exhibition.* (Mar. 16-19, 2011). (Abstract #0327).

(Continued)

*Primary Examiner* — Diana B Johannsen
(74) *Attorney, Agent, or Firm* — Cooley LLP; Cynthia A. Kozakiewicz; Ivor R. Elrifi

(57) ABSTRACT

An improved method and kit of determining whether a patient is predisposed to having severe periodontal disease and/or having high risk of progression of periodontal disease, comprising the steps of (i) taking a biological sample from said patient; (ii) genotyping said biological sample for genetic polymorphism pattern comprising IL 1B (rs16944), IL 1B (rs1143623) and IL 1B (rs4848306); and (iii) comparing said genetic polymorphism patterns to a reference composite genotype pattern; wherein the similarity of said genetic polymorphism patterns to said reference pattern indicate said patient's predisposition to having severe periodontal disease and/or having high risk of progression of periodontal disease.

10 Claims, No Drawings

(56) References Cited

OTHER PUBLICATIONS

Ahern et al., "Biochemical, Reagents Kits Offer Scientists Good Return on Investment", The Scientist, Jul. 24, 1995, p. 20, vol. 9(15), The Scientist, Philadelphia, PA.

Chen et al., "Single nucleotide polymorphisms in the human interleukin-1B gene affect transcription according to haplotype context", Human Molecular Genetics, 2006, pp. 519-529, vol. 15(4), Oxford University Press.

Grigoriadou et al., "Interleukin-1 as a genetic marker for periodontitis: Review of the literature", Quintessence International, Jun. 2010, pp. 517-525, vol. 41.

Lee et al., "Novel interleukin 1β polymorphism increased the risk of gastric cancer in a Korean population", Journal of Gastroenterology, 2004, pp. 429-433, vol. 39, Springer Verlag.

Rogus et al., "IL1B gene promotor haplotype pairs predict clinical levels of interleukin-1β and C-reactive Protein", Human Genetics, 2008, pp. 387-398, vol. 123, Springer.

* cited by examiner

METHOD FOR DETERMINING SEVERITY AND PROGRESSION OF PERIODONTAL DISEASE

RELATED APPLICATIONS

This patent application is a continuation application of U.S. application Ser. No. 13/316,198, filed Dec. 9, 2011, which claims priority to U.S. Provisional Patent Application Nos. 61/452,157, filed on Mar. 13, 2011 and 61/421,628, filed on Dec. 9, 2010, the content of each of which is incorporated herein by reference in its entirety.

FIELD OF THE INVENTION

The present invention relates generally to an improved method for determining a patient's risk of severe periodontal disease and/or risk of periodontal disease progression and a kit for use in such an improved method.

BACKGROUND OF THE INVENTION

Gingivitis is an early stage of the periodontal disease where the gums may become red, swollen and bleed easily. Gingivitis is usually painless and, if not treated, can advance to periodontitis, which may be classified by the magnitude of tissue destruction as mild, moderate, or severe. Periodontitis is primarily a disease of adults and is usually not detectable until after the age of 35. Usually bacteria that are present in dental plaque initiate periodontal disease. Toxins produced by the bacteria in the plaque activate the body's inflammatory and other immune mechanisms which ultimately lead to the destruction of the bone and gum tissue that support the teeth. As the disease progresses, the gums pull away from the teeth and periodontal pockets are formed which provide a protected environment for the bacteria, thereby causing the cycle to continue. However, some sites do not continue to be active. U.S. Pat. No. 5,328,829 discloses a method for determination of active periodontal disease sites within the oral cavity by measuring interleukin IL-1.beta. at the site. Smoking has been associated with an increased prevalence and severity of periodontitis. However, a significant number of individuals with periodontitis have never smoked.

For the past 15 years, there has been evidence that certain forms of periodontitis that affect young children and teenagers are genetically determined. These diseases, which are of extremely low prevalence in the population, produce severe periodontitis in some individuals before the age of puberty and in other individuals between puberty and age 18. The genetic factors that were identified in those cases involved very overt biologic mechanisms that most likely would predispose the individual to multiple health problems. To date, efforts to find the same types of genetic factors in adult forms of periodontitis have not been successful.

Genetic testing for disease prediction has been made possible (see U.S. Pat. Nos. 4,582,788 and 5,110,920) for diseases associated with or caused by one to two genes, once the genes are identified, to determine the risk of a person carrying a given gene for the disease (see for example U.S. Pat. Nos. 4,801,531, 4,666,828 and 5,268,267).

A genetic testing kit was developed to predicts risk for periodontal diseases using two variations in the human genome, one located in ILIA gene (ILIA+4845) and the other in IL1B gene (IL1B+3954). Carriers of at least one copy of the minor allele in each of these gene variations have increased susceptibility to periodontal disease. See U.S. Pat. No. 5,686,246. However, such a test has a limited utility in some ethnic populations and the test identifies only a small portion of people who are at risk for periodontal diseases in those populations. There is the need to find more sensitive method of determining risks of periodontal disease in all ethnic populations.

BRIEF SUMMARY OF THE INVENTION

The present invention is directed to a method of determining whether a patient is predisposed to having severe periodontal disease and/or having high risk of progression of periodontal disease, comprising the steps of (i) taking a biological sample from said patient; (ii) genotyping said biological sample for genetic polymorphism pattern comprising IL 1B (rs16944), IL 1B (rs1143623) and IL 1B (rs4848306); and (iii) comparing said genetic polymorphism patterns to a reference composite genotype pattern; wherein the similarity of said genetic polymorphism patterns to said reference pattern indicate said patient's predisposition to having severe periodontal disease and/or having high risk of progression of periodontal disease.

The present invention is also directed to a testing kit for determining whether a patient is predisposed to having severe periodontal disease and/or having high risk of progression of periodontal disease, comprising (i) biological sample collection means; (ii) a means for determining genetic polymorphism pattern; and (iii) a control sample containing IL 1B (rs16944), IL 1B (rs1143623), IL 1B (rs4848306) and IL 1B ((rs1143633).

The contents of the patents and publications cited herein and the contents of documents cited in these patents and publications are hereby incorporated herein by reference to the extent permitted.

DETAILED DESCRIPTION

The invention relates to the discovery of a polymorphism in the IL-1B gene which is associated with susceptibility to periodontal disease. Accordingly, ascertainment of genotype at this polymorphism provides a useful genetic test for susceptibility to periodontal disease.

As used herein, "Asian" means people whose ancestral homes are in one of the countries in Asia, including, but is not limited to China, India, Japan, regardless of where they live currently. "African" means people whose ancestral homes are in one of the countries in African regardless of where they live currently.

Reactions and manipulations involving DNA techniques, unless stated otherwise, were performed as described in Sambrook et al., 1989, Molecular Cloning: A Laboratory Manual, Cold Spring Harbor Laboratory Press, incorporated herein by reference. Methodology as set forth in U.S. Pat. Nos. 4,666, 828; 4,801,531; and 5,272,057 and McDowell et al., 1995 are also used unless stated otherwise. Genotyping was performed by either Taqman™ assay or using PCR with subsequent single base extension.

Provided herein is a method of determining whether a patient is predisposed to having severe periodontal disease and/or having high risk of progression of periodontal disease, comprising the steps of (i) taking a biological sample from said patient; (ii) genotyping said biological sample for genetic polymorphism pattern comprising IL 1B (rs16944), IL 1B (rs1143623) and IL 1B (rs4848306); and (iii) comparing said genetic polymorphism pattern to a reference composite genotype pattern; wherein the similarity of said genetic polymorphism patterns to said reference pattern indicate said patient's predisposition to having severe periodontal disease and/or having high risk of progression of periodontal disease.

Also provided herein is a method of determining whether a patient is predisposed to having severe periodontal disease and/or having high risk of progression of periodontal disease, comprising the steps of (i) taking a biological sample from said patient; (ii) genotyping said biological sample for genetic polymorphism pattern comprising IL 1B (rs16944), IL 1B (rs1143623) and IL 1B (rs4848306), wherein the presence of one of the genetic polymorphism patterns listed in Tables 4-6 indicates said patient's predisposition to having severe periodontal disease and/or having high risk of progression of periodontal disease.

In a preferred embodiment, the genetic polymorphism pattern is selected from the group consisting of (B1B1 and IL1B3877=1.1), B2B3, B2B4, B3B3, B3B4, B4B4, (B1B4 and IL1B3877=1.1), (B2B4 and IL1B3877=1.1), (B3B4 and IL1B3877=1.1), (B4B4 and IL1B3877=1.1), (B2B3 and IL1B3877=1.1), (B3B3 and IL1B3877=1.1), B1B1, B1B4, (B2B4 and IL1B3877=2.*), (B4B4 and IL1B3877=2.*), (B3B4 and IL1B3877=2.*), (IL1B 3737=1.1 and IL1B3877=1.1), B2B2, B1B3, (B1B3 and 3877=1.1), (B2B2 and 3877=1.1), and IL1B3877=1.1.

In a preferred embodiment, the genetic polymorphism pattern in Caucasian population is selected from the group consisting of (B1B1 and IL1B3877=1.1), B2B3, B2B4, B3B3, B3B4, B4B4, (B1B4 and IL1B3877=1.1), (B2B4 and IL1B3877=1.1), (B3B4 and IL1B3877=1.1), (B4B4 and IL1B3877=1.1), (B2B3 and IL1B3877=1.1), (B3B3 and IL1B3877=1.1), B1B1, B1B4, (B2B4 and IL1B3877=2.*), (B4B4 and IL1B3877=2.*), (B3B4 and IL1B3877=2.*), and (IL1B 3737=1.1 and IL1B3877=1.1).

In another preferred embodiment, the genetic polymorphism pattern in African population is selected from the group consisting of (B1B1 and IL1B3877=1.1), B2B3, B2B4, B3B3, B3B4, B4B4, (B1B4 and IL1B3877=1.1), B1B1, (B3B4 and IL1B3877=1.1), (B3B4 and IL1B3877=2.*), (B2B4 and IL1B3877=1.1), (B4B4 and IL1B3877=1.1), and (B1B4 and IL1B3877=1.1).

In another preferred embodiment, the genetic polymorphism pattern in Chinese population is selected from the group consisting of B2B2, B1B3, (B 1B3 and 3877=1.1), (B2B2 and 3877=1.1), and IL1B3877=1.1.

Definition of IL1B Haplotypes:

The haplotypes most commonly found are represented numerically as described in the table below showing the allele at each of the SNPs:

| Haplotype | IL1B(−511) | IL1B(−1464) | IL1B(−3737) |
|---|---|---|---|
| B1 | 1 (C) | 1 (G) | 2 (T) |
| B2 | 2 (T) | 2 (C) | 1 (C) |
| B3 | 1 (C) | 1 (G) | 1 (C) |
| B4 | 2 (T) | 1 (G) | 1 (C) |

Definition of IL1B Composite Genotypes:

The composite genotypes of IL1B gene can be defined by the conventional alleles. Two composite genotype patterns are shown below as examples.

| diplotype | Genotype | | | |
|---|---|---|---|---|
| | RS16944 IL-1B (−511) | RS1143623 IL-1B (−1464) | RS4848306 IL-1B (−3737) | RS1143633 IL-1B (+3877) |
| SNP | | | | |
| B1B1 | C/C | G/G | T/T | — |
| B1B4 +3877 1.1 | C/T | G/G | C/T | G/G |
| B2B3 | C/T | G/C | C/C | — |
| B2B4 | T/T | G/C | C/C | — |
| B3B3 | C/C | G/G | C/C | — |
| B3B4 | C/T | G/G | C/C | — |
| B4B4 | T/T | G/G | C/C | — |

| diplotype | Genotype | | | |
|---|---|---|---|---|
| | RS16944 IL-1B (−511) | RS1143623 IL-1B (−1464) | RS4848306 IL-1B (−3737) | RS1143633 IL-1B (+3877) |
| SNP | | | | |
| B1B1 | C/C | G/G | T/T | — |
| B1B4 +3877 1.1 | C/T | G/G | C/T | G/G |
| B2B3 | C/T | G/C | C/C | — |
| B2B4 | T/T | G/C | C/C | — |
| B3B3 | C/C | G/G | C/C | — |
| B3B4 +3877 1.1 | C/T | G/G | C/C | G/G |
| B4B4 | T/T | G/G | C/C | — |

In a preferred embodiment of the method, the biological sample is selected from the group consisting of saliva, buccal cells, blood, tissue samples and urine.

In another preferred embodiment, the method is for determining whether said patient is predisposed to having severe periodontal disease or for determining said patient's risk of progression of periodontal disease. Preferably the patient is Caucasian, African, Chinese or of other ethnicities.

The present invention has identified IL1 SNPs and haplotypes that are highly prevalent in all major ethnic populations. Specific composite genotypes were significantly associated with more severe periodontitis in Caucasians, African-Americans and Chinese. Any difference between ethnic groups may be caused by different gene-gene interactions between ethnic groups may contribute to these different findings and that the gene-environment interactions may differ between ethnic groups.

In another preferred embodiment of the test kit, the patient is Caucasian, African, Chinese or of other ethnicities. This kit may contain one or more oligonucleotides, including 5' and 3' oligonucleotides that hybridize 5' and 3' to at least one allele of an IL-1 locus haplotype. PCR amplification oligonucleotides should hybridize between 25 and 2500 base pairs apart, preferably between about 100 and about 500 bases apart, in order to produce a PCR product of convenient size for subsequent analysis.

Suitable primers for the detection of a human polymorphism in these genes can be readily designed using this sequence information and standard techniques known in the art for the design and optimization of primers sequences. Optimal design of such primer sequences can be achieved, for example, by the use of commercially available primer selection programs such as Primer 2.1, Primer 3 or GeneFisher (See also, Nicklin M. H. J., Weith A. Duff G. W., "A Physical Map of the Region Encompassing the Human Interleukin-1α, interleukin-1β, and Interleukin-1 Receptor Antagonist Genes" Genomics 19: 382 (1995); Nothwang H. G., et al. "Molecular Cloning of the Interleukin-1 gene Cluster: Construction of an Integrated YAC/PAC Contig and a partial transcriptional Map in the Region of Chromosome 2q13"

Genomics 41: 370 (1997); Clark, et al. (1986) Nucl. Acids. Res., 14:7897-7914 [published erratum appears in Nucleic Acids Res., 15:868 (1987) and the Genome Database (GDB) project at the URL gdb.org).

For use in a kit, oligonucleotides may be any of a variety of natural and/or synthetic compositions such as synthetic oligonucleotides, restriction fragments, cDNAs, synthetic peptide nucleic acids (PNAs), and the like. The assay kit and method may also employ labeled oligonucleotides to allow ease of identification in the assays. Examples of labels which may be employed include radio-labels, enzymes, fluorescent compounds, streptavidin, avidin, biotin, magnetic moieties, metal binding moieties, antigen or antibody moieties, and the like.

The kit may, optionally, also include DNA sampling means. DNA sampling means are well known to one of skill in the art and can include, but not be limited to substrates, such as filter papers, the AmpliCard™ (University of Sheffield, Sheffield, England S10 2JF; Tarlow, J W, et al., J. of Invest. Dermatol. 103:387-389 (1994)) and the like; DNA purification reagents such as Nucleon™ kits, lysis buffers, proteinase solutions and the like; PCR reagents, such as 10× reaction buffers, thermostable polymerase, dNTPs, and the like; and allele detection means such as the HinfI restriction enzyme, allele specific oligonucleotides, degenerate oligonucleotide primers for nested PCR from dried blood. Instructions (e.g., written, tape, VCR, CD-ROM, etc.) for carrying out the assay may be included in the kit.

Detection of Alleles

Many methods are available for detecting specific alleles at human polymorphic loci. The preferred method for detecting a specific polymorphic allele will depend, in part, upon the molecular nature of the polymorphism. For example, the various allelic forms of the polymorphic locus may differ by a single base-pair of the DNA. Such single nucleotide polymorphisms (or SNPs) are major contributors to genetic variation, comprising some 80% of all known polymorphisms, and their density in the human genome is estimated to be on average 1 per 1,000 base pairs. SNPs are most frequently biallelic—occurring in only two different forms (although up to four different forms of an SNP, corresponding to the four different nucleotide bases occurring in DNA, are theoretically possible). Nevertheless, SNPs are mutationally more stable than other polymorphisms, making them suitable for association studies in which linkage disequilibrium between markers and an unknown variant is used to map disease-causing mutations. In addition, because SNPs typically have only two alleles, they can be genotyped by a simple plus/minus assay rather than a length measurement, making them more amenable to automation.

A variety of methods are available for detecting the presence of a particular single nucleotide polymorphic allele in an individual. Advancements in this field have provided accurate, easy, and inexpensive large-scale SNP genotyping. Most recently, for example, several new techniques have been described including dynamic allele-specific hybridization (DASH), microplate array diagonal gel electrophoresis (MADGE), pyrosequencing, oligonucleotide-specific ligation, the TaqMan system as well as various DNA "chip" technologies such as the Affymetrix SNP chips. These methods require amplification of the target genetic region, typically by PCR. Still other newly developed methods, based on the generation of small signal molecules by invasive cleavage followed by mass spectrometry or immobilized padlock probes and rolling-circle amplification, might eventually eliminate the need for PCR. Several of the methods known in the art for detecting specific single nucleotide polymorphisms are summarized below. The method of the present invention is understood to include all available methods.

In a merely illustrative embodiment, the method includes the steps of (i) collecting a sample of cells from a patient, (ii) isolating nucleic acid (e.g., genomic, mRNA or both) from the cells of the sample, (iii) contacting the nucleic acid sample with one or more primers which specifically hybridize 5' and 3' to at least one allele of an IL-1 proinflammatory haplotype under conditions such that hybridization and amplification of the allele occurs, and (iv) detecting the amplification product. These detection schemes are especially useful for the detection of nucleic acid molecules if such molecules are present in very low numbers.

In a preferred embodiment of the subject assay, the allele of an IL-1 proinflammatory haplotype is identified by alterations in restriction enzyme cleavage patterns. For example, sample and control DNA is isolated, amplified (optionally), digested with one or more restriction endonucleases, and fragment length sizes are determined by gel electrophoresis.

Definitions

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only not intended to be limiting. Other features and advantages of the invention will be apparent from the following detailed description and claims.

For the purposes of promoting an understanding of the embodiments described herein, reference will be made to preferred embodiments and specific language will be used to describe the same. The terminology used herein is for the purpose of describing particular embodiments only, and is not intended to limit the scope of the present invention. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth.

The term "allele" refers to the different sequence variants found at different polymorphic regions. For example, IL-1RN (VNTR) has at least five different alleles. The sequence variants may be single or multiple base changes, including without limitation insertions, deletions, or substitutions, or may be a variable number of sequence repeats.

The term "allelic pattern" refers to the identity of an allele or alleles at one or more polymorphic regions. For example, an allelic pattern may consist of a single allele at a polymorphic site, as for IL-1RN (VNTR) allele 1, which is an allelic pattern having at least one copy of IL-1 RN allele 1 at the VNTR of the IL-1RN gene loci. Alternatively, an allelic pattern may consist of either a homozygous or heterozygous state at a single polymorphic site. For example, IL-1-RN (VNTR) allele 2,2 is an allelic pattern in which there are two copies of the second allele at the VNTR marker of IL-1RN that corresponds to the homozygous IL-RN (VNTR) allele 2 state. Alternatively, an allelic pattern may consist of the identity of alleles at more than one polymorphic site.

The terms "control", "control sample" or "reference" refer to any sample appropriate to the detection technique employed. The control sample may contain the products of the allele detection technique employed or the material to be tested. Further, the controls may be positive or negative controls. By way of example, where the allele detection technique is PCR amplification, followed by size fractionation, the control sample may comprise DNA fragments of an appropriate size. Likewise, where the allele detection technique involves detection of a mutated protein, the control sample may comprise a sample of a mutant protein. However, it is preferred that the control sample comprises the material to be tested. For example, the controls may be a sample of genomic DNA or a cloned portion of the IL-1 gene cluster. However, where the sample to be tested is genomic DNA, the control sample is preferably a highly purified sample of genomic DNA.

The term "haplotype" as used herein is intended to refer to a set of alleles that are inherited together as a group (are in linkage disequilibrium) at statistically significant levels ($P_{corr}$<0.05). As used herein, the phrase "an IL-1 haplotype" refers to a haplotype in the IL-1 loci. An IL-1 inflammatory or proinflammatory haplotype refers to a haplotype that is indicative of increased agonist and/or decreased antagonist activities.

The terms "IL-1 gene cluster" and "IL-1 loci" as used herein include all the nucleic acid at or near the 2q13 region of chromosome 2, including at least the IL-1A, IL-1B and IL-1RN genes and any other linked sequences. (Nicklin et al., Genomics 19: 382-84, 1994). The terms "IL-1A", "IL-1B", and "IL-1RN" as used herein refer to the genes coding for IL-1 alpha, IL-1 beta, and IL-1 receptor antagonist, respectively. The gene accession number for IL-1A, IL-1B, and IL-1RN are X03833, X04500, and X64532, respectively.

"IL-1 X (Z) allele Y" refers to a particular allelic form, designated Y, occurring at an IL-1 locus polymorphic site in gene X, wherein X is IL-1 A, B, or RN and positioned at or near nucleotide Z, wherein nucleotide Z is numbered relative to the major transcriptional start site, which is nucleotide +1, of the particular IL-1 gene X. As further used herein, the term "IL-1 X allele (Z)" refers to all alleles of an IL-1 polymorphic site in gene X positioned at or near nucleotide Z. For example, the term "IL-1RN (+2018) allele" refers to alternative forms of the IL-1RN gene at marker +2018. "IL-1RN (+2018) allele 2" refers to a form of the IL-1RN gene which contains a cytosine (C) at position +2018 of the sense strand. Clay et al., Hum. Genet. 97:723-26, 1996. "IL-1RN (+2018) allele 1" refers to a form of the IL-1 RN gene which contains a thymine (T) at position +2018 of the plus strand. When a subject has two identical IL-1RN alleles, the subject is said to be homozygous, or to have the homozygous state. When a subject has two different IL-1RN alleles, the subject is said to be heterozygous, or to have the heterozygous state. The term "IL-1RN (+2018) allele 2,2" refers to the homozygous IL-1RN (+2018) allele 2 state. Conversely, the term "IL-1RN (+2018) allele 1,1" refers to the homozygous IL-1RN (+2018) allele 1 state. The term "IL-1RN (+2018) allele 1,2" refers to the heterozygous allele 1 and 2 state.

Alternatively, an allele is named by the nucleotide at the polymorphic site. For example, "IL-1RN (+2018) allele T" refers to a form of the IL-1 RN gene which contains a thymine (T) at position +2018 of the plus strand.

"Increased risk" refers to a statistically higher frequency of occurrence of the disease or condition in an individual carrying a particular polymorphic allele in comparison to the frequency of occurrence of the disease or condition in a member of a population that does not carry the particular polymorphic allele.

The term "isolated" as used herein with respect to nucleic acids, such as DNA or RNA, refers to molecules separated from other DNAs, or RNAs, respectively, that are present in the natural source of the macromolecule. For example, an isolated nucleic acid encoding one of the subject IL-1 polypeptides preferably includes no more than 10 kilobases (kb) of nucleic acid sequence which naturally immediately flanks the IL-1 gene in genomic DNA, more preferably no more than 5 kb of such naturally occurring flanking sequences, and most preferably less than 1.5 kb of such naturally occurring flanking sequence. The term isolated as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to polypeptides which are isolated from other cellular proteins and is meant to encompass both purified and recombinant polypeptides.

A "non-human animal" of the invention includes mammals such as rodents, non-human primates, sheep, dogs, cows, goats, etc. amphibians, such a s members of the Xenopus genus, and transgenic avians (e.g. chickens, birds, etc.). The term "chimeric animal" is used herein to refer to animals in which the recombinant gene is found, or in which the recombinant gene is expressed in some but not all cells of the animal. The term "tissue-specific chimeric animal" indicates that one of the recombinant IL-1 genes is present and/or expressed or disrupted in some tissues but not others. The term "non-human mammal" refers to any member of the class Mammalia, except for humans.

As used herein, the term "nucleic acid" refers to polynucleotides or oligonucleotides such as deoxyribonucleic acid (DNA), and, where appropriate, ribonucleic acid (RNA). The term should also be understood to include, as equivalents, analogs of either RNA or DNA made from nucleotide analogs (e.g. peptide nucleic acids) and as applicable to the embodiment being described, single (sense or antisense) and double-stranded polynucleotides.

The term "polymorphism" refers to the coexistence of more than one form of a gene or portion (e.g., allelic variant) thereof. A portion of a gene of which there are at least two different forms, i.e., two different nucleotide sequences, is referred to as a "polymorphic region of a gene". A specific genetic sequence at a polymorphic region of a gene is an allele. A polymorphic region can be a single nucleotide, the identity of which differs in different alleles. A polymorphic region can also be several nucleotides long.

The term "propensity to disease," also "predisposition" or "susceptibility" to disease or any similar phrase, means that certain alleles are hereby discovered to be associated with or predictive of a subject's incidence of developing a particular disease (e.g. a periodontal disease). The alleles are thus over-represented in frequency in individuals with disease as compared to healthy individuals. Thus, these alleles can be used to predict disease even in pre-symptomatic or pre-diseased individuals.

The term "wild-type allele" refers to an allele of a gene which, when present in two copies in a subject results in a wild-type phenotype. There can be several different wild-type alleles of a specific gene, since certain nucleotide changes in a gene may not affect the phenotype of a subject having two copies of the gene with the nucleotide changes.

Genetic screening (also called genotyping or molecular screening), can be broadly defined as testing to determine if a patient has mutations (alleles or polymorphisms) that either cause a disease state or are "linked" to the mutation causing a disease state. Linkage refers to the phenomenon that DNA sequences which are close together in the genome have a tendency to be inherited together. Two sequences may be linked because of some selective advantage of co-inheritance. More typically, however, two polymorphic sequences are co-inherited because of the relative infrequency with which meiotic recombination events occur within the region between the two polymorphisms. The co-inherited polymorphic alleles are said to be in linkage disequilibrium with one another because, in a given human population, they tend to either both occur together or else not occur at all in any particular member of the population. Indeed, where multiple polymorphisms in a given chromosomal region are found to be in linkage disequilibrium with one another, they define a quasi-stable genetic "haplotype." In contrast, recombination events occurring between two polymorphic loci cause them to become separated onto distinct homologous chromosomes. If meiotic recombination between two physically linked polymorphisms occurs frequently enough, the two polymorphisms will appear to segregate independently and are said to be in linkage equilibrium.

The severity of periodontal disease refers to the amount of periodontal ligament fibers that have been lost, termed clinical attachment loss. According to the American Academy of Periodontology, the classification of severity is as follows:
Mild: 1-2 mm of attachment loss
Moderate: 3-4 mm of attachment loss
Severe: >5 mm of attachment loss.

The following example is given as specific illustrations of the invention. It should be understood, however, that the invention is not limited to the specific details set forth in the examples. All parts and percentages in the examples, as well as in the remainder of the specification, are by weight unless otherwise specified.

Further, any range of numbers recited in the specification or paragraphs hereinafter describing or claiming various aspects of the invention, such as that representing a particular set of properties, units of measure, conditions, physical states or percentages, is intended to literally incorporate expressly herein by reference or otherwise, any number falling within such range, including any subset of numbers or ranges subsumed within any range so recited.

The term "about" when used as a modifier for, or in conjunction with, a variable, is intended to convey that the numbers and ranges disclosed herein are flexible and that practice of the present invention by those skilled in the art using temperatures, concentrations, amounts, contents, carbon numbers, and properties that are outside of the range or different from a single value, will achieve the desired result, namely, an improved method of determining a patient's risk of severe periodontal disease and/or risk of periodontal disease progression and a kit for use in such an improved method.

EXAMPLES

Example 1

Allelic and haplotypic frequencies for IL1 SNPs were compared across major ethnic groups: Caucasians (DARIC, N=767); African Americans (DARIC, N=156); Chinese 1 (N=300); Chinese 2 (N=1,000); and Indian (N=644). SNPs and haplotypes with high multi-ethnic frequency were identified. Single SNPs, haplotypes, and composite genotypes were then analyzed for association with periodontitis severity in Caucasians by logistic regression models adjusted for smoking. Patterns associated with disease in Caucasians were then evaluated in African-Americans.

SNPs with high frequency in all ethnic groups included the previously identified functional SNPs in the IL1B promoter (rs16944, rs1143623, rs4848306) and another IL1B SNP (rs1143633). Four IL1B promoter haplotypes (B1-B4) predominated with B3 and B4 having very different frequencies across ethnicities. Multiple composite genotypes in the IL1B gene were associated with severe periodontitis and elevated gingival fluid IL1β in Caucasians. When further tested in African Americans, the composite genotypes, B1B1 or (B1B4 and IL1B3877=1.1) or B2B3 or B2B4 or B3B3 or B3B4 or B4B4, were also significantly associated with severe periodontitis (p=0.003 and 0.043 for Caucasians and African Americans, respectively). A similar pattern, B1B1 or (B1B4 and IL1B3877=1.1) or B2B3 or B2B4 or B3B3 or (B3B4 and IL1B3877=1.1) or B4B4, was also significantly associated with severe periodontitis (p=0.009 and 0.044 for Caucasians and African Americans, respectively).

Example 2

This was a case control study. Severe periodontitis and controls were defined using a composite index consisting of clinical attachment level and pocket depth. We analyzed 749 Caucasian subjects, 153 African Americans, and 270 Chinese (see Table 1). On average, the case to control ratio was about 1:2 for the three ethnic groups examined in this study.

TABLE 1

| Study subjects | | | |
|---|---|---|---|
| | Case | Control | Total |
| Caucasian | 270 | 479 | 749 |
| African American | 51 | 102 | 153 |
| Chinese | 89 | 181 | 270 |

There are eleven IL-1 genes that determine IL-1 biological activity. Nine of them are clustered on chromosome 2, the other 2 are located on chromosomes 9 and 11. For the periodontal tissue, IL1B gene is most relevant. So we initially focused on this gene. We scanned the entire IL1B gene region and identified 4 functional variations. These are single nucleotide polymorphisms or SNPs. All four functional SNPs are located in the promoter region, at position −31, −511, −1464, and −3737. Two of these SNPs, −31 and −511, are 100% concordant and only one was included in the analysis.

The three functional SNPs form eight possible haplotypes. Four of them, named B1 through B4, account for more than 95% of all haplotypes observed in major ethnic groups. These four common haplotypes in turn form ten possible diplotypes or haplotype pairs. The results of the analysis are summarized in Tables 2 and 3. It should be noted that the frequency of these haplotypes or diplotypes is different between ethnic populations.

TABLE 2

IL1B haplotypes

| Haplotype | IL 1B (−511) | IL 1B (−1464) | IL 1B (−3737) |
|---|---|---|---|
| B1 | 1 | 1 | 2 |
| B2 | 2 | 2 | 1 |
| B3 | 1 | 1 | 1 |
| B4 | 2 | 1 | 1 |

TABLE 3

IL1B diplotypes

| Diplotype | IL 1B (−511) | IL 1B (−1464) | IL 1B (−3737) |
|---|---|---|---|
| B1B1 | 1.1 | 1.1 | 2.2 |
| B1B2 | 1.2 | 1.2 | 1.2 |
| B1B3 | 1.1 | 1.1 | 1.2 |
| B1B4 | 1.2 | 1.1 | 1.2 |
| B2B2 | 2.2 | 2.2 | 1.1 |
| B2B3 | 1.2 | 1.2 | 1.1 |
| B2B4 | 2.2 | 1.2 | 1.1 |
| B3B3 | 1.1 | 1.1 | 1.1 |
| B3B4 | 1.2 | 1.1 | 1.1 |
| B4B4 | 2.2 | 1.1 | 1.1 |

These haplotypes/diplotypes are functional and they influence the clinical levels of the inflammatory markers IL-1beta and CRP. For example, some diplotypes including B3B3, B2B3, and B3B4 are associated with increased levels of both IL-1beta and CRP. While some diplotypes, including B1B1 and B1B3, are only associated with increased levels of IL-1beta. Interestingly, the effect of these haplotypes on IL1-beta expression may be context-dependent. For example, B2 haplotype was associated with lower levels of IL1-beta in gingival crevicular fluid. But, in an in vitro analysis, this haplotype was associated with the highest levels of promoter activity.

Example 3

Based on their effect on inflammatory biomarkers, we developed candidate genotype patterns to test for association with the clinical outcome of severe periodontitis. To develop these genotype patterns, we first selected diplotypes associated with higher levels of IL-1beta. We then refined the genotype patterns according to the genotypes of another SNP called IL1B3877 (rs1143633). This SNP is associated with increased levels of the inflammatory marker CRP in Asian populations.

We tested these patterns for association with severe periodontitis in each of the three ethnic groups. Table 4 lists the patterns that are associated with several periodontitis in Caucasians. Some of these patterns are similar and share a subset of identical genotypes. For African Americans, the patterns associated with severe periodontitis are listed in Table 5. Some of these patterns are also associated with severe disease in Caucasians. There are 5 patterns associated with severe periodontitis in Chinese, as shown in Table 6. These patterns are different from those observed in African Americans or Caucasians. Composite genotype patterns associated with severe periodontitis in Caucasians, African Americans and Chinese are listed in Tables 4, 5, and 6, respectively.

TABLE 4

Composite genotype patterns associated with severe periodontitis in Caucasians.

| IL1B genotype pattern | Unadjusted OR (95% CI) | P | Adjusted for smoking OR (95% CI) | P |
|---|---|---|---|---|
| (B1B1 and IL1B3877 = 1.1) or B2B3 or B2B4 or B3B3 or B3B4 or B4B4 or (B1B4 and IL1B3877 = 1.1) | 1.65 (1.16-2.34) | 0.0052 | 1.60 (1.12-2.29) | 0.0093 |
| (B1B1 and IL1B3877 = 1.1) or B2B3 or B3B3 or (B1B4 and IL1B3877 = 1.1) or (B2B4 and IL1B3877 = 1.1) or (B3B4 and IL1B3877 = 1.1) or (B4B4 and IL1B3877 = 1.1) | 1.64 (1.14-2.34) | 0.0071 | 1.60 (1.11-2.30) | 0.011 |
| (B2B3 and IL1B3877 = 1.1) or (B3B3 and IL1B3877 = 1.1) or (B3B4 and IL1B3877 = 1.1) | 1.72 (1.12-2.65) | 0.0126 | 1.65 (1.07-2.55) | 0.0233 |
| B1B1 or B3B3 or B2B3 | 1.54 (1.12-2.11) | 0.0075 | 1.50 (1.09-2.07) | 0.0123 |
| B1B1 or B3B3 or B3B4 | 1.45 (1.03-2.03) | 0.0307 | 1.38 (0.99-1.94) | 0.0615 |
| B1B1 or (B1B4 and IL1B3877 = 1.1) or B2B3 or B2B4 or B3B3 or (B3B4 and IL1B3877 = 1.1) or B4B4 | 1.61 (1.16-2.25) | 0.0043 | 1.56 (1.12-2.18) | 0.0088 |
| B1B1 or B1B4 or B2B3 or (B2B4 and IL1B3877 = 2.*) or B3B3 or B3B4 or (B4B4 and IL1B3877 = 2.*) | 1.66 (1.20-2.31) | 0.0024 | 1.62 (1/16-2.26) | 0.0046 |
| B1B1 or B1B4 or B2B3 or B2B4 or B3B3 or (B3B4 and IL1B3877 = 2.*) or (B4B4 and IL1B3877 = 2.*) | 1.71 (1.23-2.38) | 0.0014 | 1.68 (1.20-2.34) | 0.0023 |
| B1B1 or B1B4 or B2B3 or B2B4 or B3B3 or B3B4 or (B4B4 and IL1B3877 = 2.*) | 1.77 (1.27-2.47) | 0.0007 | 1.72 (1.23-2.40) | 0.0015 |

TABLE 4-continued

Composite genotype patterns associated with severe periodontitis in Caucasians.

| IL1B genotype pattern | Unadjusted OR (95% CI) | P | Adjusted for smoking OR (95% CI) | P |
|---|---|---|---|---|
| B1B1 or B2B3 or (B2B4 and IL1B3877 = 2.*) or B3B3 or B3B4 or B4B4 or (B1B4 and IL1B3877 = 1.1) | 1.56 (1.12-2.17) | 0.0079 | 1.50 (1.08-2.10) | 0.016 |
| B1B1 or B2B3 or B2B4 or (B3B3 or (B3B4 and IL1B3877 = 2.*) or B4B4 or (B1B4 and IL1B3877 = 1.1) | 1.60 (1.15-2.22) | 0.0051 | 1.56 (1.12-2.17) | 0.0087 |
| B1B1 or B2B3 or B2B4 or B3B3 or B3B4 or (B4B4 and IL1B3877 = 2.*) or (B1B4 and IL1B3877 = 1.1) | 1.68 (1.21-2.34) | 0.0018 | 1.62 (1.16-2.26) | 0.0045 |
| B1B1 or B2B3 or B3B3 or (B1B4 and IL1B3877 = 1.1) or (B2B4 and IL1B3877 = 1.1) or (B3B4 and IL1B3877 = 1.1) or (B4B4 and IL1B3877 = 1.1) | 1.64 (1.19-2.25) | 0.0022 | 1.59 (1.16-2.19) | 0.0044 |
| B1B1 or B3B3 or B2B3 or B3B4 | 1.61 (1.18-2.21) | 0.0027 | 1.56 (1.14-2.14) | 0.006 |
| B2B3 or B2B4 or B3B3 or B3B4 or B4B4 or (B1B4 and IL1B3877 = 1.1) | 1.65 (1.15-2.36) | 0.0059 | 1.60 (1.12-2.30) | 0.0104 |
| B2B3 or B3B3 or (B1B4 and IL1B3877 = 1.1) or (B2B4 and IL1B3877 = 1.1) or (B3B4 and IL1B3877 = 1.1) or (B4B4 and IL1B3877 = 1.1) | 1.64 (1.13-2.36) | 0.008 | 1.60 (1.11-2.32) | 0.0125 |
| B2B3 or B3B3 or (B3B4 and ILB3877 = 1.1) | 1.65 (1.12-2.43) | 0.0109 | 1.60 (1.08-2.36) | 0.0193 |
| B2B3 or B3B3 or B3B4 | 1.69 (1.16-2.48) | 0.0065 | 1.63 (1.11-2.40) | 0.0126 |
| B3B3 or B2B3 or B2B4 or B1B1 or B3B4 or B4B4 | 1.66 (1.22-2.27) | 0.0014 | 1.60 (1.17-2.20) | 0.0033 |
| B3B3 or B2B3 or B2B4 or B1B1 or B3B4 or B4B4 or (B1B4 and IL1B3877 = 1.1) | 1.66 (1.21-2.28) | 0.0015 | 1.61 (1.17-2.21) | 0.0033 |
| IL1B 3737 = 1.1 and IL1B3877 = 1.1 | 1.53 (1.04-2.25) | 0.0313 | 1.49 (1.01-2.19) | 0.0467 |

Note:

a. *means either allele 1 or allele 2 b. Refer to Table 3 for description of the IL1B diplotypes (B1B1, B1B2, B1B3, B1B4, B2B2, B2B3, B2B4, B3B3, B3B4, and B4B4).

c. "IL1B3737 = 1.1 and IL1B3877 = 1.1" means having genotype 1.1 at both IL1B3737 and IL1B3877 loci.

d. If there is an "and" between an IL1B diplotype and an IL1B3877 genotype, it means having the respective diplotype and genotype at the two loci. For example, "B1B1 and IL1B3877 = 1.1" means that an individual carries diplotype B1B1 at the IL1B promoter region and genotype 1.1 at the IL1B3877 locus.

TABLE 5

Composite genotype patterns associated with severe periodontitis in African Americans.

| IL1B genotype pattern | Unadjusted OR (95% CI) | P | Adjusted for smoking OR (95% CI) | P |
|---|---|---|---|---|
| (B1B1 and IL1B3877 = 1.1) or B2B3 or B2B4 or B3B3 or B3B4 or B4B4 or (B1B4 and IL1B3877 = 1.1) | 2.44 (1.04-5.72) | 0.0038 | 2.28 (0.96-5.41) | 0.061 |
| B1B1 or (B1B4 and IL1B3877 = 1.1) or B2B3 or B2B4 or B3B3 or (B3B4 and IL1B3877 = 1.1) or B4B4 | 2.70 (1.10-6.60) | 0.0266 | 2.57 (1.03-6.41) | 0.0435 |
| B1B1 or B2B3 or B2B4 or (B3B3 or (B3B4 and IL1B3877 = 2.*) or B4B4 or (B1B4 and IL1B3877 = 1.1) | 2.82 (1.11-7.19) | 0.026 | 2.69 (1.04-6.94) | 0.0408 |
| B1B1 or B2B3 or B3B3 or (B1B4 and IL1B3877 = 1.1) or (B2B4 and IL1B3877 = 1.1) or (B3B4 and IL1B3877 = 1.1) or (B4B4 and IL1B3877 = 1.1) | 2.29 (0.99-5.28) | 0.0497 | 2.15 (0.92-5.00) | 0.077 |

TABLE 5-continued

Composite genotype patterns associated with severe periodontitis in African Americans.

| | Unadjusted | | Adjusted for smoking | |
|---|---|---|---|---|
| IL1B genotype pattern | OR (95% CI) | P | OR (95% CI) | P |
| B3B3 or B2B3 or B2B4 or B1B1 or B3B4 or B4B4 or (B1B4 and IL1B3877 = 1.1) | 2.77 (1.10-6.98) | 0.027 | 2.62 (1.03-6.64) | 0.0428 |
| IL1B3737 = 2.* and IL1B3877 = 2.* | 0.261 (0.082-0.837) | 0.0181 | 0.27 (0.085-0.88) | 0.0296 |

Note:
a. *means either allele 1 or allele 2
b. For description of the IL1B diplotypes (B1B1, B1B2, B1B3, B1B4, B2B2, B2B3, B2B4, B3B3, B3B4, and B4B4), refer to Table 3.
c. "IL1B3737 = 2.* and IL1B3877 = 2.*" means having genotype 2.1 or 2.2 at both IL1B3737 and IL1B3877 loci.
d. If there is an "and" between an IL1B diplotype and an IL1B3877 genotype, it means having the respective diplotype and genotype at the two loci. For example, "B1B1 and IL1B3877 = 1.1" means that an individual carries diplotype B1B1 at the IL1B promoter region and genotype 1.1 at the IL1B3877 locus.

TABLE 6

Composite genotype patterns associated with severe periodontitis in Chinese.

| | Unadjusted | | Adjusted for smoking | |
|---|---|---|---|---|
| IL1B genotype pattern | OR (95% CI) | P | OR (95% CI) | P |
| B2B2 | 2.03 (1.02-4.01) | 0.0406 | 2.38 (1.10-5.17) | 0.0285 |
| B1B3 or B2B2 | 2.26 (1.20-4.26) | 0.0105 | 2.08 (1.01-4.28) | 0.0472 |
| B2B2 and 3877 = 1.1 | 2.38 (0.93-6.10) | 0.0629 | 2.96 (1.04-8.41) | 0.0414 |
| (B1B3 and 3877 = 1.1) or (B2B2 and 3877 = 1.1) | 2.65 (1.06-6.67) | 0.0324 | 3.30 (1.19-9.13) | 0.0217 |
| IL1B3877 = 1.1 | 1.74 (0.88-3.43) | 0.108 | 2.24 (1.03-4.86) | 0.0416 |

Note:
a. Refer to Table 3 for description of the IL1B diplotypes (B1B1, B1B2, B1B3, B1B4, B2B2, B2B3, B2B4, B3B3, B3B4, and B4B4).
b. If there is an "and" between an IL1B diplotype and an IL1B3877 genotype, it means having the respective diplotype and genotype at the two loci.

Example 4

To further test the association between IL-1 gene variations and severe periodontitis, we examined the possible interaction between IL-1 genetics and smoking in periodontitis. As shown in table 7 below, carriers of one or two risk factors, IL-1 genotype positive or smoking, have highly significantly increased risk for severe periodontitis, compared to those who carry none of these risk factors. The p values are less than 0.0001.

TABLE 7

IL-1 gene variations interact with smoking to influence risk for severe periodontitis.

| Test Group | | Reference | | | |
|---|---|---|---|---|---|
| Genotype | Smoking | Genotype | Smoking | OR | P |
| + | + | − | − | 2.85(1.86-4.38) | <0.0001 |
| Genotype + and/or Smoking + | | − | − | 1.93(1.37-2.71) | 0.0001 |
| + | + | − | + | 1.70(1.14-2.52) | 0.008 |
| + | + | + | − | 1.87(1.13-3.08) | 0.01 |
| − | + | − | − | 1.68(1.15-2.46) | 0.007 |

Note:
genotype: (B1B1 and IL1B3877 = 1.1) or (B1B4 and IL1B3877 = 1.1) or B2B3 or B2B4 or B3B3 or B3B4 or B4B4

After confirming the effect of the two risk factors, we then looked at the influence of IL-1 genotypes on severe periodontitis in smokers only. Smokers who are genotype positive have increased risk for severe periodontitis compared to smokers who are genotype negative. These findings indicate that IL-1 gene variations interact with smoking to influence the risk for severe periodontitis.

In conclusion, we have shown that specific functional IL-1 gene variations are associated with severe periodontitis in major ethnic groups. In addition, we demonstrate that IL-1 gene variations interact with smoking to influence the risk for severe periodontitis.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art, without departing from the spirit of the invention.

What is claimed is:
1. A method comprising the follow steps:
   (i) obtaining a biological sample from a patient who does not have severe periodontal disease;
   (ii) isolating a nucleic acid sample from said biological sample;
   (iii) contacting said nucleic acid sample with oligonucleotide primers that hybridize 5' and 3' to each of the following single nucleotide polymorphisms (SNPs) in the IL1B gene: rs16944 C/T; rs1143623 G/C; and rs4848306 C/T;
   (iv) amplifying nucleic acid in said nucleic acid sample with said oligonucleotide primers to produce one or more amplified fragments, wherein each of said SNPs is included in at least one of said one or more amplified fragments;

(v) detecting the number of copies of allele 1 and allele 2 of each of said SNPs in said one or more amplified fragments, wherein as a result of said detecting, the presence of one of the following composite genotypes is detected in said patient:

a) one copy rs16944 allele 1 (C), one copy rs1143623 allele 1 (G), and two copies of rs4848306 allele 1 (C);

b) two copies of rs16944 allele 2 (T), one copy of rs1143623 allele 1 (G), and two copies of rs4848306 allele 1 (C);

c) two copies of rs16944 allele 1 (C), two copies of rs1143623 allele 1 (G), and two copies of rs4848306 allele 1 (C);

d) one copy of rs16944 allele 1 (C), two copies of rs1143623 allele 1 (G), and two copies of rs4848306 allele 1 (C);

e) two copies of rs16944 allele 2 (T), two copies of rs1143623 allele 1 (G), and two copies of rs4848306 allele 1 (C); and (vi) treating the patient of step (v), in whom one of the composite genotypes a)-e) has been detected, with a treatment regimen to slow down the progression of periodontal disease.

2. A method comprising the follow steps:
(i) obtaining a biological sample from a patient who does not have severe periodontal disease;
(ii) isolating a nucleic acid sample from said biological sample;
(iii) contacting said nucleic acid sample with oligonucleotide primers that hybridize 5' and 3' to each of the following single nucleotide polymorphisms (SNPs) in the IL 1B gene: rs16944 C/T; rs1143623 G/C; rs4848306 C/T, and rs1143633 G/A;
(iv) amplifying nucleic acid in said nucleic acid sample with said oligonucleotide primers to produce one or more amplified fragments, wherein each of said SNPs is included in at least one of said one or more amplified fragments;
(v) detecting the number of copies of allele 1 and allele 2 of each of said SNPs in said one or more amplified fragments, wherein as a result of said detecting, the presence of one of the following composite genotypes is detected in said patient:

f) two copies of ID B rs16944 allele 1 (C), two copies of rs1143623 allele 1 (G), two copies of rs4848306 allele 2 (T), and two copies of rs1143633 allele 1 (G);

g) one copy of rs16944 allele 1 (C), two copies of rs1143623 allele 1 (G), one copy of rs4848306 allele 2 (T), and two copies of rs1143633 allele 1 (G); and (vi) treating the patient of step (v), in whom one of the composite genotypes f) or g) has been detected, with a treatment regimen to slow down the progression of periodontal disease.

3. The method of claim 1 or claim 2, wherein said patient is a smoker.

4. The method of claim 1 or claim 2, wherein said amplifying in step (iv) comprises a polymerase reaction.

5. The method of claim 4, wherein the polymerase reaction is PCR.

6. The method of claim 1 or claim 2, wherein at least one of said oligonucleotide primers of step (iii) is a labeled oligonucleotide primer.

7. The method of claim 6, wherein said labeled oligonucleotide primer comprises a radiolabel, an enzyme label, a fluorescent compound, a streptavidin, an avidin, a biotin, a magnetic moiety, an antigen, or an antibody moiety.

8. The method of claim 1 or claim 2, wherein the detecting in step (v) comprises use of at least one allele-specific oligonucleotide.

9. The method of claim 8, wherein said allele-specific oligonucleotide comprises a radiolabel, an enzyme label, a fluorescent compound, a streptavidin, an avidin, a biotin, a magnetic moiety, an antigen, or an antibody moiety.

10. The method of claim 1 or claim 2, wherein the method comprises the use of a TaqMane® assay.

* * * * *